(12) United States Patent
Edson et al.

(10) Patent No.: US 8,548,744 B1
(45) Date of Patent: *Oct. 1, 2013

(54) COMPUTER-IMPLEMENTED CELLULAR MODELING HAVING PARALLEL PATHWAYS

(75) Inventors: Patrick Edson, West Newton, MA (US); Ricardo Paxson, Boston, MA (US)

(73) Assignee: The MathWorks, Inc, Natick, MA (US)

( * ) Notice: Subject to any disclaimer, the term of this patent is extended or adjusted under 35 U.S.C. 154(b) by 570 days.

This patent is subject to a terminal disclaimer.

(21) Appl. No.: 11/889,273

(22) Filed: Aug. 10, 2007

Related U.S. Application Data

(63) Continuation of application No. 11/647,359, filed on Dec. 29, 2006.

(51) Int. Cl.
*G06F 19/00* (2011.01)
*G06F 19/12* (2011.01)

(52) U.S. Cl.
USPC .......................................................... 702/19

(58) Field of Classification Search
None
See application file for complete search history.

(56) References Cited

U.S. PATENT DOCUMENTS 5,930,154 A * 7/1999 Thalhammer-Reyero ...... 703/11

OTHER PUBLICATIONS

Andrews et al. (Phys. Biol., vol. 1, p. 137-151. 2004).*
Kurata et al. (Nucleic Acids Research, vol. 31, No. 14, p. 4071-4084, 2003).*
Kreft et al. ( Microbiology (1998), 144, 3275-3287).*
Arakelyan et al. (Angiogenesis 5: 203-214, 2002).*
Hatzikirou et al. (Mathematical Models and Methods in Applied Sciences vol. 15, No. 11 (2005) 1779-1794).*
Duarte et al. (Genome Research (2004) vol. 14, pp. 1298-1309).*
Hucka et al. Bioinformatics (2003) vol. 19, No. 4, pp. 524-531.*
Matsuno et al., "Experimental Observations and Simulations by Genomic Object Net of Notch Signaling in *Drosophila* Multicellular Systems", *Genome Informatics* 13: 453-454 (2002).
"BioPax: Biological Pathways Exchange" [online] http://www.biopax.org (2 pgs), retrieved Nov. 21, 2007.
"Systems Biology Markup Language" [online] http://sbml.org/index.psp (3 pgs), retrieved Nov. 21, 2007.
"Teranode Biological Modeler" [online] www.teranode.com (1 pg), retrieved Nov. 21, 2007.
"Gepasi" [online] www.gepasi.org, Sep. 4, 2002; (2 pgs), retrieved Nov. 21, 2007.
"Systems Biology Workbench—Core Development" [online] http://sbw.sourceforge.net (5 pgs), retrieved Nov. 21, 2007.

* cited by examiner

*Primary Examiner* — Lori A Clow
(74) *Attorney, Agent, or Firm* — Venable LLP; Michael A. Sartori; Todd R. Farnsworth

(57) ABSTRACT

A computer-implemented method for cellular modeling is provided. The computer-implemented method for cellular modeling may include generating a cellular model, the model comprising a plurality of compartments, each compartment comprising at least one reaction, at least one species, or a combination of at least one reaction and at least one species; receiving a selection of at least one compartment for simulation to obtain at least one selected compartment; simulating the at least one selected compartment to obtain a result; and providing an output of the result from simulating the compartment; wherein at least two of the compartments comprise parallel pathways through the cellular model.

24 Claims, 14 Drawing Sheets

COMPUTER-IMPLEMENTED CELLULAR MODELING HAVING PARALLEL PATHWAYS

This application is a continuation of U.S. patent application Ser. No. 11/647,359 filed Dec. 29, 2006, the contents of which are incorporated herein by reference.

BACKGROUND

With the emergence of synthetic biology and nanotechnology, systematic alteration of existing cells to produce modified cells is becoming a frequent research goal. However, designing these modified cells may be very challenging in vitro because it often requires expensive and laborious cellular assays. These modified cells are also dangerous; they could have an unpredictable and potentially devastating impact on any ecosystem they might enter. Thus, given the cost and potential danger of designing synthetic cells, a method and system of modeling both natural and synthetically modified cells in silico is desired.

Moreover, there is a need for in silico methods of modeling the effects of chemical compounds and biologic compounds on a natural or synthetically modified cell. Testing of chemical compounds on cells in vitro involves the expense of cellular media and proliferation assays, the constant labor of maintaining cell cultures, and repeating each assay with a different chemical compound to generate data. These procedures are costly and time consuming. Thus, there is a need for a method of modeling cells or a portion of a cell under different conditions in silico rather than in vitro.

Traditional in silico models are based on computer programs capable of modeling a single portion of a cell or a single cell, for example, those programs using the single hierarchical pathway systems of Biopax or SBML. These models may be constraining because a user has to generate a new model for each type of cell or portion of a cell to run a simulation. Further, if a user is interested in altering a portion of a cell to run new simulations, the user may have to deconstruct the model to do so.

SUMMARY

Some embodiments are directed to computer-implemented methods for cellular modeling comprising: generating a cellular model, the model comprising a plurality of compartments, each compartment comprising at least one reaction, at least one species, or a combination of at least one reaction and at least one species; receiving a selection of at least one compartment for simulation to obtain at least one selected compartment; simulating the at least one selected compartment to obtain a result; and providing an output of the result from simulating the compartment; wherein at least two of the compartments comprise parallel pathways through the cellular model.

Further, some embodiments are directed to computer-readable media comprising a program for a computer-implemented method of cellular modeling, the method comprising: generating a cellular model, the model comprising a plurality of compartments, each compartment comprising at least one reaction, at least one species, or a combination of at least one reaction and at least one species; receiving a selection of at least one compartment for simulation to obtain at least one selected compartment; simulating the at least one selected compartment to obtain a result; and providing an output of the result from simulating the compartment; wherein at least two of the compartments comprise parallel pathways through the cellular model.

Further still, some embodiments are directed to computer-implemented systems for cellular modeling comprising: means for generating a cellular model, the model comprising a plurality of compartments, each compartment comprising at least one reaction, at least one species, or a combination of at least one reaction and at least one species; means for receiving a selection of at least one compartment for simulation to obtain at least one selected compartment; means for simulating the at least one selected compartment to obtain a result; and means for providing an output of the result from simulating the compartment; wherein at least two of the compartments comprise parallel pathways through the cellular model.

DEFINITIONS

Figure 1:
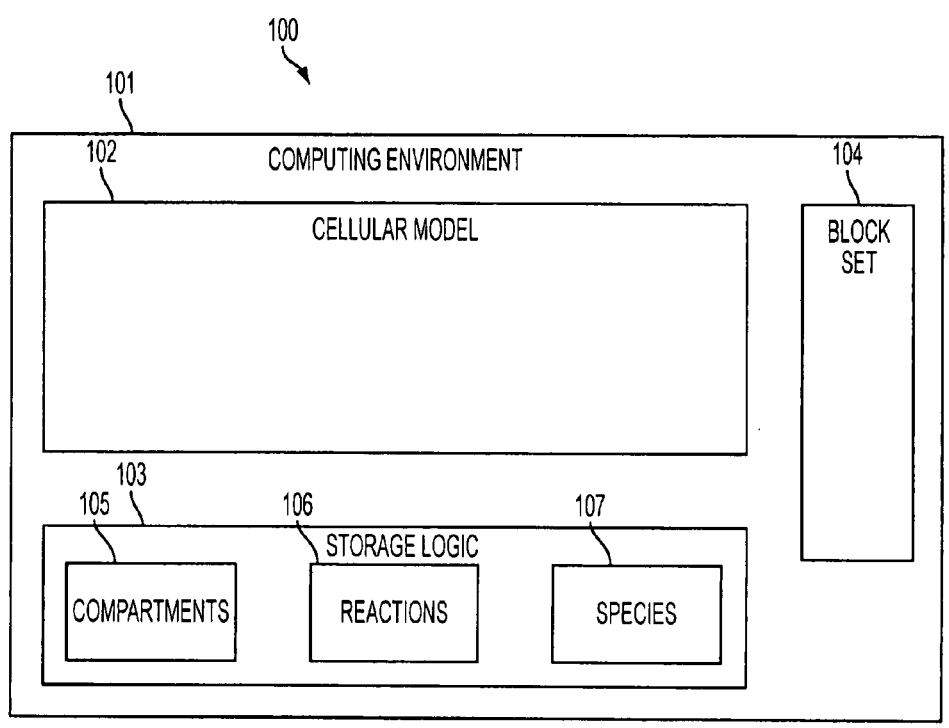
FIG. 1 illustrates an exemplary embodiment of a computer architecture for implementing a method of cellular modeling.

In describing the invention, the following definitions are applicable throughout (including above).

A "computer" may refer to one or more apparatus and/or one or more systems that are capable of accepting a structured input, processing the structured input according to prescribed rules, and producing results of the processing as output. Examples of a computer may include: a computer; a stationary and/or portable computer; a computer having a single processor, multiple processors, or multi-core processors, which may operate in parallel and/or not in parallel; a general purpose computer; a supercomputer; a mainframe; a super mini-computer; a mini-computer; a workstation; a micro-computer; a server; a client; an interactive television; a web appliance; a telecommunications device with Internet access; a hybrid combination of a computer and an interactive television; a portable computer; a tablet personal computer (PC);

a personal digital assistant (PDA); a portable telephone; application-specific hardware to emulate a computer and/or software, such as, for example, a digital signal processor (DSP), a field-programmable gate array (FPGA), an application specific integrated circuit (ASIC), an application specific instruction-set processor (ASIP), a chip, chips, or a chip set; a system-on-chip (SoC) or a multiprocessor system-on-chip (MPSoC); an optical computer; and an apparatus that may accept data, may process data in accordance with one or more stored software programs, may generate results, and typically may include input, output, storage, arithmetic, logic, and control units.

"Software" may refer to prescribed rules to operate a computer. Examples of software may include: software; code segments; instructions; applets; pre-compiled code; compiled code; computer programs; and programmed logic.

A "computer-readable medium" may refer to any storage device used for storing data accessible by a computer. Examples of a computer-readable medium may include: a magnetic hard disk; a floppy disk; an optical disk, such as a CD-ROM and a DVD; a magnetic tape; a memory chip; and/or other types of media that can store machine-readable instructions thereon.

A "computer system" may refer to a system having one or more computers, where each computer may include a computer-readable medium embodying software to operate the computer. Examples of a computer system may include: a distributed computer system for processing information via computer systems linked by a network; two or more computer systems connected together via a network for transmitting and/or receiving information between the computer systems; and one or more apparatuses and/or one or more systems that may accept data, may process data in accordance with one or more stored software programs, may generate results, and typically may include input, output, storage, arithmetic, logic, and control units.

A "network" may refer to a number of computers and associated devices that may be connected by communication facilities. A network may involve permanent connections such as cables or temporary connections such as those that may be made through telephone or other communication links. A network may further include hard-wired connections (e.g., coaxial cable, twisted pair, optical fiber, waveguides, etc.) and/or wireless connections (e.g., radio frequency waveforms, free-space optical waveforms, acoustic waveforms, etc.). Examples of a network may include: an internet, such as the Internet; an intranet; a local area network (LAN); a wide area network (WAN); and a combination of networks, such as an internet and an intranet. Exemplary networks may operate with any of a number of protocols, such as Internet protocol (IP), asynchronous transfer mode (ATM), and/or synchronous optical network (SONET), user datagram protocol (UDP), IEEE 802.x, etc.

A "wild-type component" may refer to a component in a cellular model constructed to represent a typical form of an organism or portion thereof as it occurs in nature, as distinguished from mutant forms.

A "cellular model" may refer to an in silico version of an actual or synthetic cell, group of cells, or portion of a cell. Examples of cellular models may include: (1) a collection of at least one compartment comprising at least one reaction, at least one species, or a combination of at least one reaction and at least one species; and (2) a collection of a plurality of compartments, each including at least one reaction, at least one species, or a combination of at least one reaction and at least one species.

A "selection of a cell" may refer to data that may be received by a computing environment to generate a cellular model. Examples of a "selection of a cell" may include: data from other cellular models, experimental data saved in a computer-readable format, or any other data capable of being imported into a computing environment.

A "compartment" may refer to a portion of the cellular model representing a physical region of the object being modeled. Examples of objects the compartment may be used to model may include: a cell's nucleus, mitochondria, cytoplasm, or other organelle. However, the general aspects of the present invention are not limited to modeling only organelles as compartments. As one of skill in the art will appreciate, a portion of a cell, a cell, or a group of cells may be designated as a compartment.

A "sub-compartment" may refer to a compartment that is located within another compartment.

A "reaction" may refer to any chemical reaction that may be modeled as part of a cell. Examples of a "reaction" may include: chemical reactions found within natural cells and chemical reactions that do not typically occur within a natural cell. However, as one of skill in the art will appreciate, the term reaction is not limited to chemical reactions and may encompass any other reaction that may be modeled.

A "species" may refer to an item that is contained within, on the surface of, or outside of a compartment. Examples of a species may include: a peptide, a polypeptide, a nucleotide, a polynucleotide, an ion, an acid, a base, a salt, or a prodrug.

The term "parallel pathways" may refer to at least two different conditions simulated within the cellular model contemporaneously.

A "cellular response pathway" may refer to a pathway within a cell that is activated or deactivated in response to a stressor or stimuli. Examples of a cellular response pathway may include: the actions taken by the cell in response to thermal stress (e.g., heat shock), pH changes, light, radiation, or other equivalent stimuli or stressor.

A "cellular metabolic pathway" may refer to a series of reactions occurring within a cell that result in either the formation of a metabolic cellular product to be used or stored in the cell or in the initiation of another metabolic pathway.

A "cellular signaling pathway" may refer to a pathway by which a cell transmits a signal to govern a cellular function. Examples of a cellular signaling pathway may include those pathways that begin with a ligand binding a receptor to cause messenger molecules to act causing a cellular action to occur. An example of such a pathway is the mitogen-activated protein kinase (MAPK) pathway. In some embodiments, a cellular signaling pathway is the set of cellular changes induced by receptor activation. However, the term "cellular signaling pathway" is not limited to intracellular pathways and may include intercellular signaling as well. For example, juxtacrine signaling between cells, e.g., the Notch signaling mechanism, is also considered a cellular signaling pathway.

A "hierarchy" may refer to an implicit or explicit system for ordering a model into levels and sublevels. Examples of a "hierarchy" may include: an explicit tree-like organization of the compartments, reactions and species and an implicit system for ordering reactions, species, and compartments. For example, if species are placed within a compartment, the compartment is implicitly the higher level, and the species are a lower level within the hierarchy for the cellular model.

A "biological product" may refer to a manufactured item that contains a group of cells, a single cell, a portion of a cell, or a product designed to affect a cell. Examples of a "biological product" may include vaccines, antibodies, RNA, DNA, proteins, cell cultures, plants, and drugs.

DETAILED DESCRIPTION

Exemplary embodiments are discussed in detail below. While specific exemplary embodiments are discussed, it should be understood that this is done for illustration purposes only. In describing and illustrating the exemplary embodiments, specific terminology is employed for the sake of clarity. However, the invention is not intended to be limited to the specific terminology so selected. A person skilled in the relevant art will recognize that other components and configurations may be used without parting from the spirit and scope of the invention. It is to be understood that each specific element includes all technical equivalents that operate in a similar manner to accomplish a similar purpose. The examples and embodiments described herein are non-limiting examples.

The various embodiments described herein provide a computer-implemented method of cellular modeling that permits multiple parallel pathways within a single cellular model. The embodiments can be implemented using a computer and/or a computer system. FIG. 1 illustrates a computer 100 that may be used to implement the cellular models described herein. The computer may be used to provide a computing environment 101. Within the computing environment, a cellular model 102, storage logic 103 and/or a block set 104 may be created and/or stored. The storage logic 103 may store aspects of the cellular model 102 and may include one or more compartments 105, one or more reactions 106, and one or more species 107.

Figure 2:
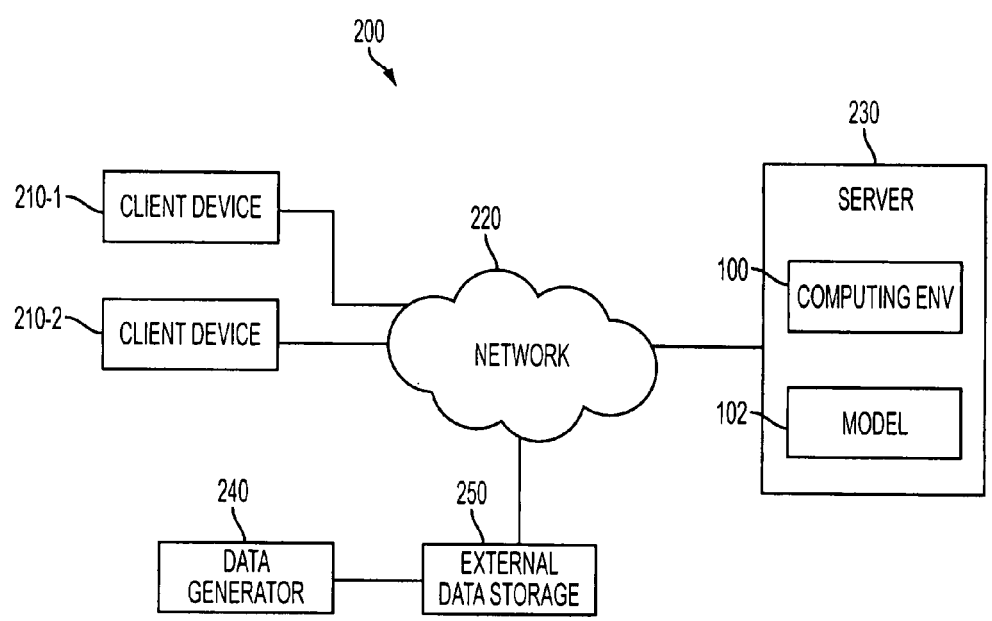
FIG. 2 illustrates an exemplary computer system that may be used to implement a method of cellular modeling.

As illustrated in FIG. 2, the various embodiments described herein may be implemented on a computer system 200. The computer system 200 may include at least one client device 210-1, 210-2 coupled to a server 230. In some embodiments, the client device 210 is coupled to the server 230 via a network 220. The server 230 may contain the computing environment 101 and/or the cellular model 102. The computer system 200 may also comprise a data generator 240 and/or an external data storage device 250. The external storage device 250 may be coupled to the client devices 210-1, 210-2 via the network 220 and may be coupled to the server 230 via the network 220.

Figure 3:
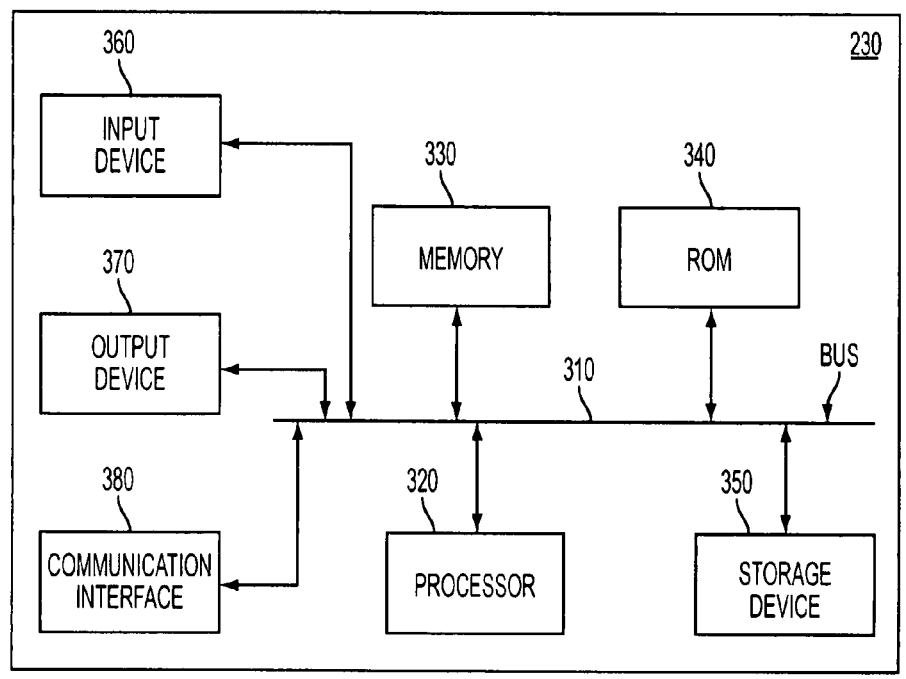
FIG. 3 illustrates an exemplary architecture that may be used to implement the server depicted in FIG. 2.

FIG. 3 illustrates an exemplary architecture for implementing server 230 of FIG. 2. It will be appreciated that other devices that can be used with system 200, such as client 210, may be similarly configured. As illustrated in FIG. 3, server 230 may include a bus 310, a processor 320, a memory 330, a read only memory (ROM) 340, a storage device 350, an input device 360, an output device 370, and a communication interface 380.

Bus 310 may include one or more interconnects that permit communication among the components of server 230. Processor 320 may include any type of processor, microprocessor, or processing logic that may interpret and execute instructions (e.g., a field programmable gate array (FPGA)). Processor 320 may include a single device (e.g., a single core) and/or a group of devices (e.g., multi-core). Memory 330 may include a random access memory (RAM) or another type of dynamic storage device that may store information and instructions for execution by processor 320. Memory 330 may also be used to store temporary variables or other intermediate information during execution of instructions by processor 320.

ROM 340 may include a ROM device and/or another type of static storage device that may store static information and instructions for processor 320. Storage device 350 may include a magnetic disk and/or optical disk and its corresponding drive for storing information and/or instructions.

Storage device 350 may include a single storage device or multiple storage devices, such as multiple storage devices operating in parallel. Moreover, storage device 350 may reside locally on server 230 and/or may be remote with respect to server 230 and connected thereto via network 220 and/or another type of connection, such as a dedicated link or channel.

Input device 360 may include any mechanism or combination of mechanisms that permit an operator to input information to server 230, such as a keyboard, a mouse, a touch sensitive display device, a microphone, a pen-based pointing device, and/or a biometric input device, such as a voice recognition device and/or a finger print scanning device. Output device 370 may include any mechanism or combination of mechanisms that outputs information to the operator, including a display, a printer, a speaker, etc.

Communication interface 380 may include any transceiver-like mechanism that enables server 230 to communicate with other devices and/or systems, such as client 210, a vendor, a government agency, a university, a research sponsor, a hospital, etc. For example, communication interface 380 may include one or more interfaces, such as a first interface coupled to network 220 and/or a second interface coupled directly to data generator 240. Alternatively, communication interface 380 may include other mechanisms (e.g., a wireless interface) for communicating via a network, such as a wireless network. In one implementation, communication interface 380 may include logic to send code to a destination device, such as a target device that can include general purpose hardware (e.g., a personal computer form factor), dedicated hardware (e.g., a digital signal processing (DSP) device adapted to execute a compiled version of a model or a part of a model), etc.

Server 230 may perform certain functions in response to processor 320 executing software instructions contained in a computer-readable medium, such as memory 330. In alternative embodiments, hardwired circuitry may be used in place of or in combination with software instructions to implement features consistent with principles of the invention. Thus, implementations consistent with principles of the invention are not limited to any specific combination of hardware circuitry and software.

Figure 4:
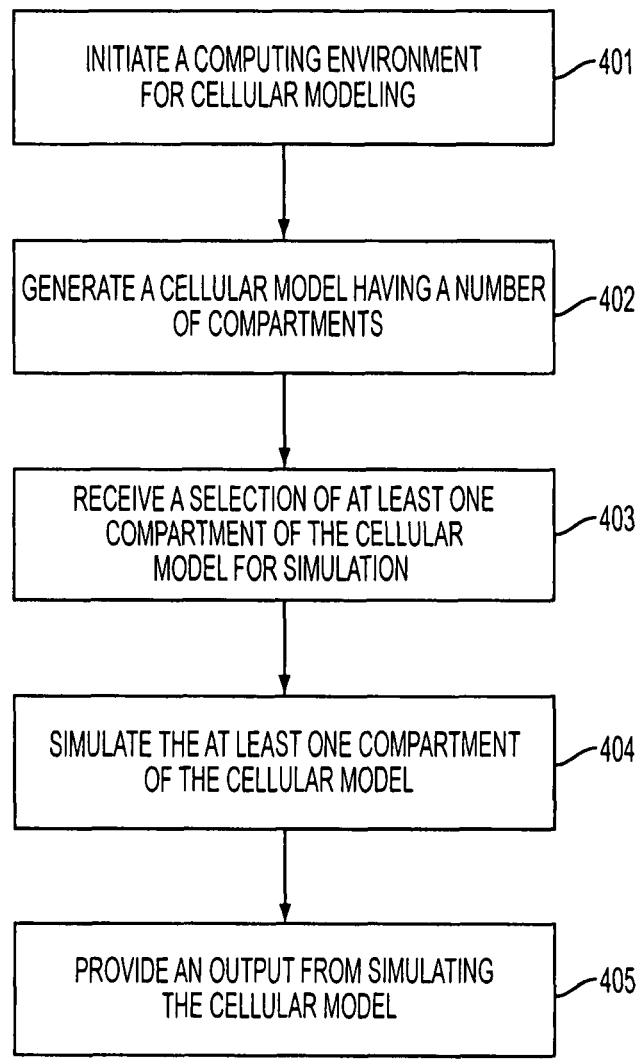
FIG. 4 illustrates an exemplary flow chart of a computer-implemented method of cellular modeling.

An exemplary flow chart for computer-implemented cellular modeling is depicted in FIG. 4. In block 401, the computing environment 101 may be initiated. The computing environment 101 may be implemented on a computer, a computer system, etc. The computing environment 101 may accessed via a network in some embodiments or may reside locally on a client device, e.g., a personal computer.

An exemplary computing environment may be based on MATLAB® software and/or SIMBIOLOGY® software, both available from The MathWorks, Inc. of Natick, Mass. Other exemplary computing environments may be based on Teranode Biological Modeler (available from www.teranode.com), Gepasi (available from www.gepasi.org), and/or SBW (available from sbw.sourceforge.net). In some embodiments, a technical computing environment may be used as the computing environment. As one of skill in the art will appreciate, any computing environment capable of supporting the techniques disclosed herein is also encompassed by the present invention.

In block 402, within the computing environment 101, the cellular model 102 may be generated. Block 402 is discussed further below with respect to FIG. 5.

In block 403, within the computing environment 101, a selection of at least one compartment of the cellular model 102 may be received. The selection may be made by a user, automatically, or by a request received by the computing environment (e.g., from another environment).

The selection of a compartment in block 403 can also be received from another modeling program. For example, a compartment for use in the cellular models described herein may be generated in another modeling program and imported into an embodiment of the cellular model generated in block 402. Examples of modeling programs that may be capable of creating a selection of a compartment for use in the present invention include: SIMULINK® and STATEFLOW®, available from The MathWorks, Inc. of Natick, Mass.

In block 404, within the computing environment 101, the selected at least one compartment of the cellular model may be simulated. The simulation may continue until, for example, the simulation reaches a predetermined end point, until the user stops the simulation, until a timeout value is encountered, etc.

In block 405, within the computing environment 101, an output from running the simulation of the cellular model in block 404 may be provided. The results of the simulation (i.e., the output) may be provided as output to be saved in any desired file format, analyzed, displayed graphically and/or textually, and/or exported to another program. Simulation results, all of which are encompassed by the present invention, may be used for substantially any number of purposes, such as scientific exploration, medical testing, education, scientific manufacturing, etc.

Figure 5:
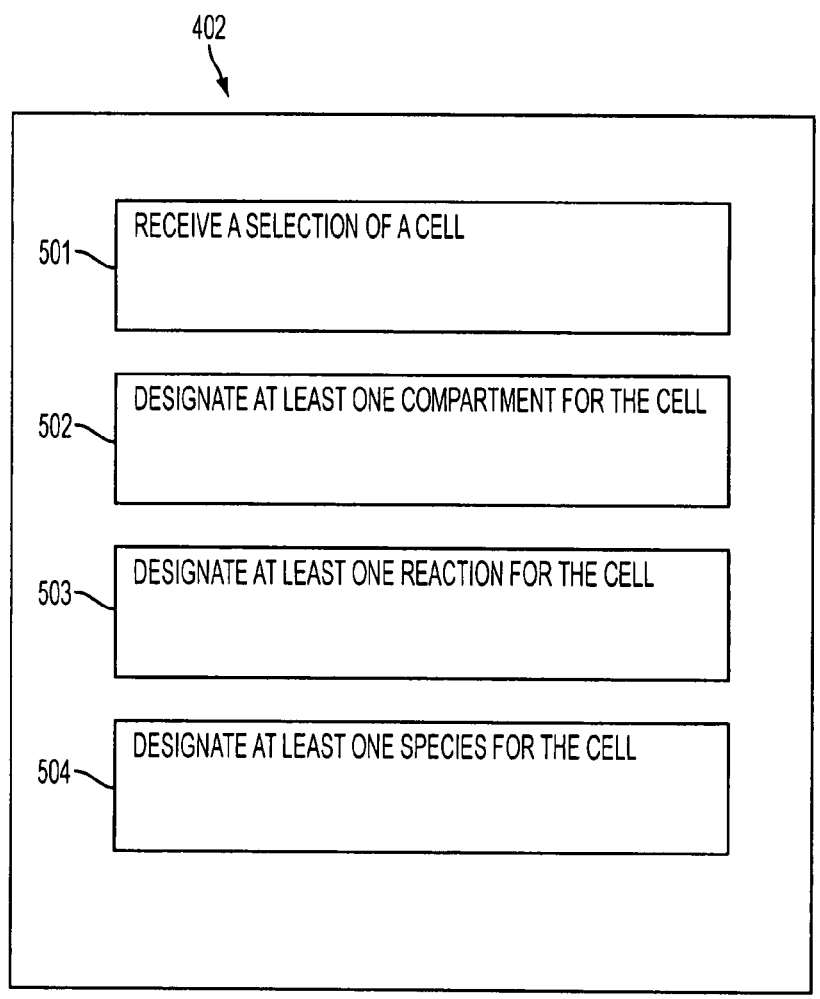
FIG. 5 illustrates an exemplary method of generating a cellular model that may be used in a computer-implemented method of cellular modeling.

In FIG. 5, an exemplary embodiment of a method for generating a cellular model in block 402 of the present invention is described. The blocks labeled in FIG. 5 may be performed in any order and are each optional depending on the exemplary implementations being practiced.

In block 501, within the computing environment 101, a selection of a cell may be received. The selection of a cell may be used to generate the cellular model 102. In some embodiments, the cellular model 102 may include no imported data.

Figure 6:
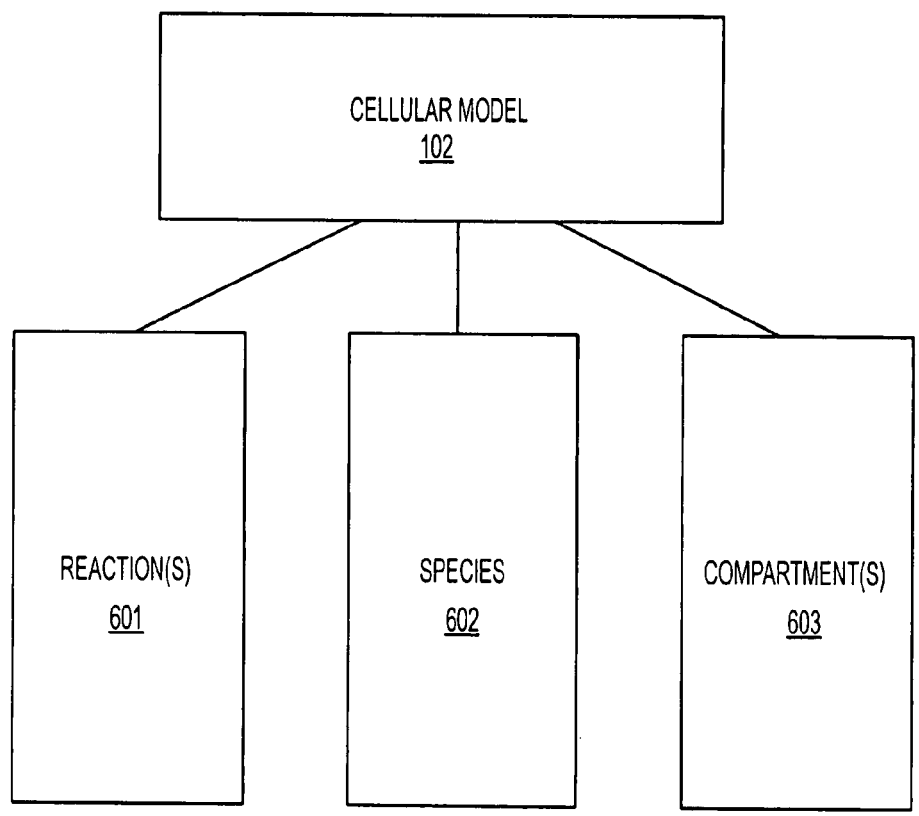
FIG. 6 illustrates an exemplary cellular model that may be used in a computer-implemented method of cellular modeling.

Referring to FIG. 6, the cellular model 102 may include a collection of data regarding a reaction or reactions 601, a collection of data regarding a species or species 602, and/or a collection of data regarding a compartment or compartments 603. The cellular model 102 is not limited to require all three types of data, and the data may be received by the cellular model 102 in any order.

In block 502, within the computing environment 101, a compartment selected from the compartments 105 in the storage logic 103 may be designated as part of the cellular model 102. In some embodiments, the cellular model 102 may include at least one compartment, or may include more than one compartment (e.g., the cellular model 102 may include at least two compartments, at least five compartments, at least 10 compartments, at least 15 compartments, more than 15 compartments, etc.). Exemplary embodiments of cellular model 102 may include any number of compartments as long as the simulation is capable of being run in block 404 to provide the output in block 405. Compartments 105 may reside locally with respect to computing environment 101 or remotely with respect to computing environment 101, such as a remote server operating on network 220.

Certain embodiments may require that minimal physical constraints be imposed on the compartments. For example, in a cellular model containing compartments A and B, if compartment B is contained within compartment A, the cellular model may receive a rule that compartment B may not contain compartment A.

In block 503, within the computing environment 101, a reaction selected from the reactions 106 in the storage logic 103 may be designated as part of the cellular model 102. Exemplary embodiments of the cellular model 102 may include any number of reactions as long as the simulation is still capable of being run in block 404 to provide the output in block 405.

In block 504, within the computing environment 101, a species selected from the species 107 in the storage logic 103 may be designated as part of the cellular model 102. The species of the present invention may be designated as being located either within a compartment, outside of a compartment, or on the surface of a compartment. For example, if a model representing a cell's nucleus has been designated as a compartment the species may be designated as being within the nucleus. An example of a species that may be designated as located within the compartment (e.g., the nucleus) is a polynucleotide. Similarly, if the compartment is representing the same nucleus, the species may be designated as located outside of the compartment. An example of a species that may be designated as located outside the compartment (e.g., the nucleus) is cytoplasmic calcium. Finally, the species may also be designated as located on the surface of the compartment. Exemplary species that may be designated as located on the surface of the compartment (e.g., the nucleus) may include nuclear pores or attached ribosomes. In some embodiments, the cellular model 102 may include at least one species, a plurality of species, or no species. Exemplary embodiments of the cellular model 102 may include any number/types of species as long as the simulation is still capable of being run in block 404 of FIG. 4 to provide the output in block 405.

The compartments of some exemplary embodiments may include a pathway through the cellular model 102. Conventional environments and/or file formats may limit the definitions of compartments, and the species contained in those compartments, to a single pathway representing an actual cell. In contrast some exemplary embodiments, at least two of the compartments in the cellular model may include parallel pathways through the cellular model. The parallel pathways that may be simulated within the cellular model may be presented in a graphical diagram via a graphical user interface and/or a command line.

To further illustrate the meaning of "parallel pathways," the following non-limiting examples are provided. All examples provided herein are illustrative and should not be construed as limiting with respect to features, implementations, techniques, etc., related to disclosed embodiments and equivalents thereof.

First Illustrative Example

Figure 7A:
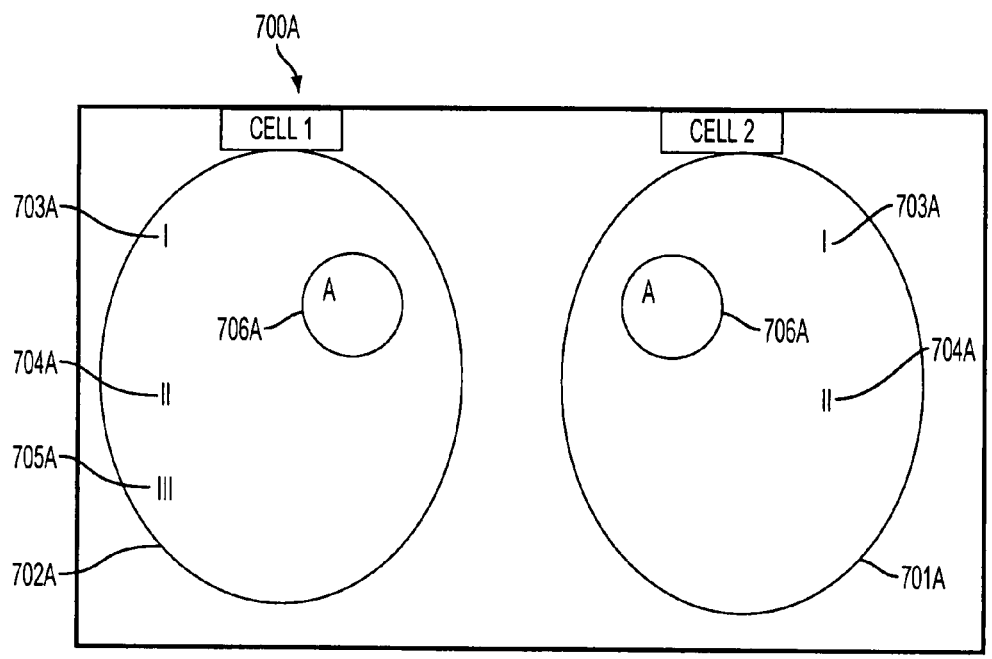
FIGS. 7A and 7B illustrate compartments that may include two parallel pathways.

In some embodiments, the two compartments including parallel pathways may model a cell in the presence of a therapeutic agent (pathway 1) and in the absence of the agent (pathway 2). For example, as depicted in FIG. 7A, a cellular model 700A may include at least one compartment 701A to represent a cell (e.g., a cancer cell). The exemplary compartment 701A includes a sub-compartment 706A and species 703A and 704A which may be run in a reaction (not shown). This compartment 701A comprises one pathway through the cellular model 700A.

Then, at least one other compartment 702A is modeled to include the components of the first compartment 701A plus a species modeling the therapeutic agent 705A. This second compartment 702A is another pathway through the cellular model 700A. Thus, parallel pathways in this illustrative embodiment represent a pathway through cellular model 700A that does not include the therapeutic agent (depicted as 701A) and the pathway that includes the therapeutic agent as a species (depicted as 702A). In some embodiments, the cellular model 700A may be simulated to produce a result that compares the effect of the addition of the therapeutic agent.

Figure 8A:
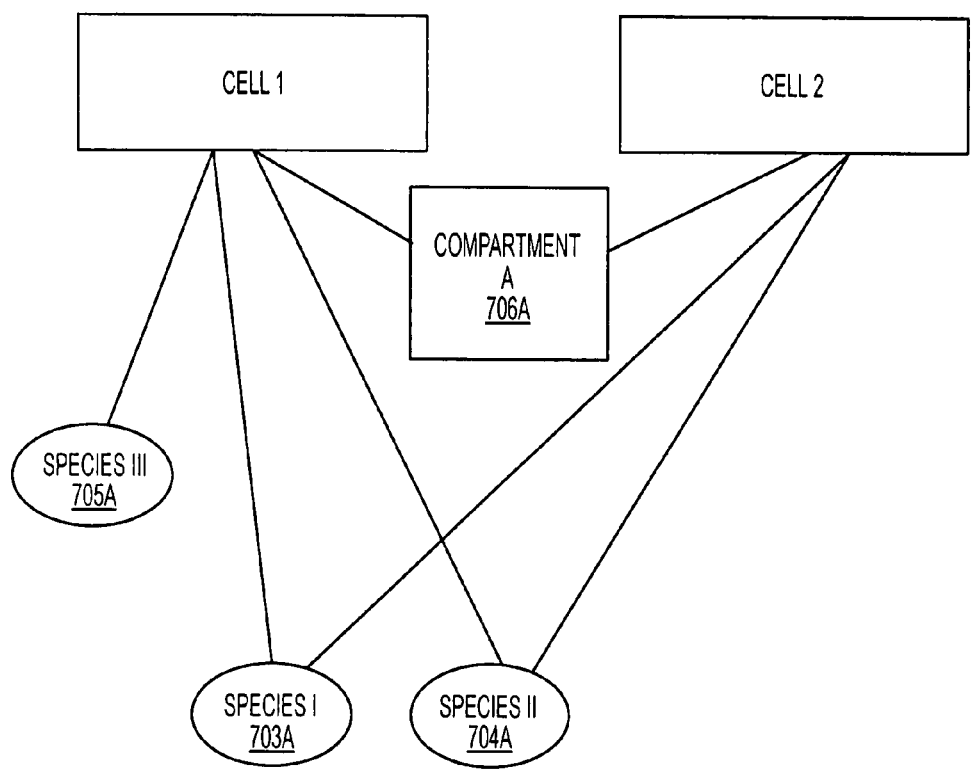
FIGS. 8A and 8B illustrate compartments that may include two parallel pathways.

FIG. 8A also depicts the cellular model of FIG. 7A to further illustrate the concept of parallel pathways. FIG. 8A shows in a tree format that compartment 706A belongs to the parallel pathway of cell 1 as well as the parallel pathway of cell 2. Further, species 703A and species 704A also belong to the parallel pathways of cells 1 and 2. However, species 705A belongs to the parallel pathway of cell 1 but not to cell 2. Thus, the parallel pathways differ in the inclusion of species 705A, but the same compartment A and species I and species II are used in both the parallel pathways.

Second Illustrative Example

Figure 7B:
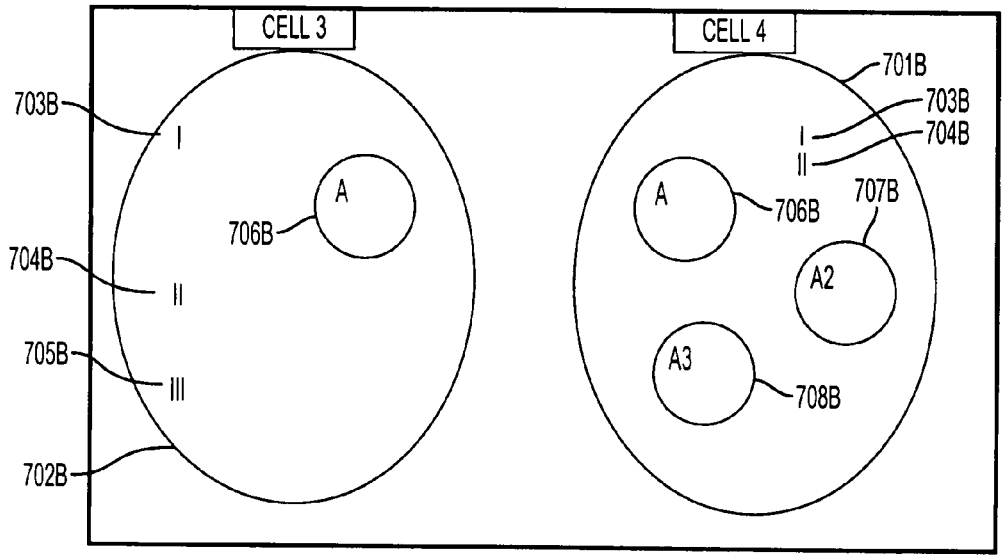

As depicted in FIG. 7B, another example of a parallel pathway may include modeling a cell as a cellular model 700B with wild-type components represented as a compartment 702B and then modeling at least one compartment with mutant or otherwise unnatural compartments, here compartment 701B. In the example depicted in FIG. 7B, the two cells 3, 4 modeled as compartments 702B, 701B contain the same two species 703B, 704B but differ in the number of sub-compartments. The wild type cell 702B illustrates a cell having a single sub-compartment 706B (e.g., a model of a mitochondria) while the mutant or otherwise altered cell 701B has the wild type sub-compartment 706B plus two additional altered forms of that sub-compartment 707B, 708B. In some embodiments, the cellular model 700B may be simulated to produce a result that compares the effect of the additional sub-compartments.

Figure 8B:
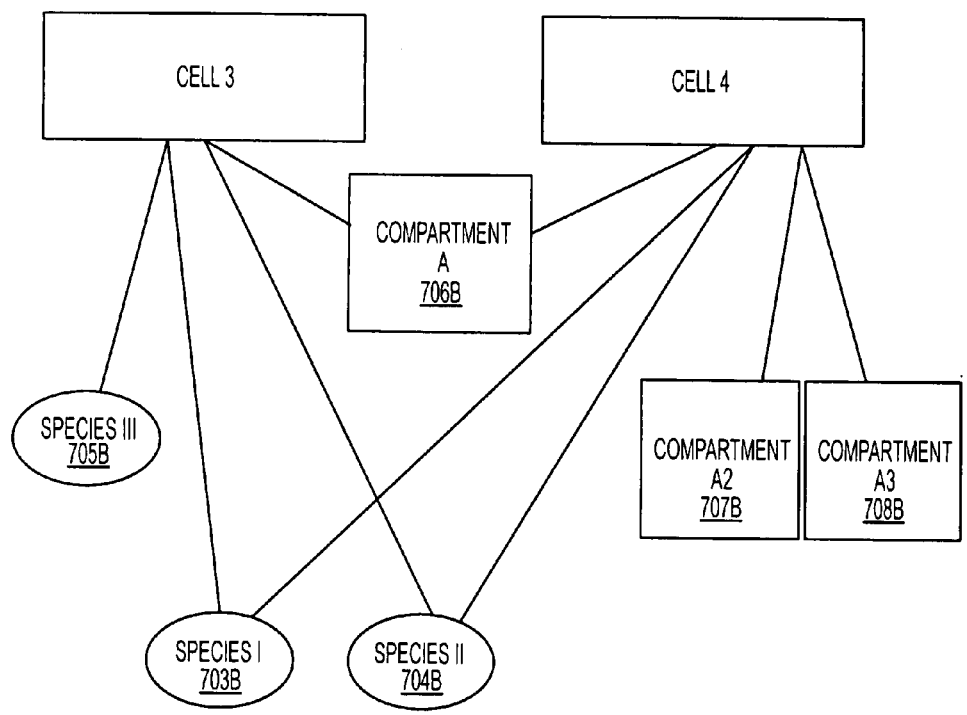

FIG. 8B depicts the cellular model of FIG. 7B to further illustrate the concept of parallel pathways. FIG. 8B shows in a tree format that compartment 706B belongs to the parallel pathway of cell 3 as well as the parallel pathway of cell 4. However, compartments 707B and 708B belong to the parallel pathway of cell 4 but not cell 3. Further, species 703B and species 704B also belong to the parallel pathway of cells 3 and 4. However, species 705B belongs to the parallel pathway of cell 3 but not to cell 4. Thus, the parallel pathways differ in the inclusion of species 705B and additional compartments 707B and 708B, but the same compartment 706B, species 703B, and species 704B are used in both the parallel pathways.

As one of skill in the art will appreciate the general aspects of cellular modeling using compartments that include parallel pathways is not limited to the above examples. For example, the parallel pathways of the cellular models may be used to simulate receptor/ligand binding, cellular responses to stress, cellular population dynamics, cell growth, cell death, or any other cellular activity.

For example, a receptor/ligand binding model may be constructed by creating a compartment representing a cell with a receptor that interacts with a ligand. A species representing the ligand may be added to the cellular model. The cellular model may be simulated to demonstrate whether receptor/ligand binding occurs and what changes result. The simulation may be run according to specified reactions or run to produce a specified reaction, e.g., to produce the receptor and ligand induced cellular signaling pathway being simulated.

A model illustrating cellular population dynamics may be constructed, for example, by creating a series of compartments, each representing a cell. These compartments may be exposed to varying amounts and types of species designed to simulate environmental conditions surrounding the cells. For example, if a species represents a nutrient essential for cellular growth, then a model with many compartments modeling cells in the presence of a small quantity of the species could be simulated to measure at least one cell's response to nutrient depravation. If more than one cell is simulated, then the population dynamics of the cells in the cellular model can be monitored.

A model illustrating cell growth may be constructed by creating at least one compartment representing a cell. For example, the at least one compartment may contain species and sub-compartments that represent the components involved in cell division (e.g., meiosis or mitosis) in specified quantities. The cellular model may be simulated to monitor changes in the quantity of the components involved in cell division in response to external or internal species to determine if cell division would occur in the cell being modeled. The occurrence of cell division may be predicted by comparing the quantities of the components involved in cell division obtained in the simulation to the amounts seen in actual wild type cells undergoing cell division. The term "cell growth" is not limited to cell division as it also encompasses the enlargement or reduction in size of a single cell.

A model illustrating cell death may be constructed by creating at least one compartment representing a cell. For example, the at least one compartment may contain species and sub-compartments that represent the components involved in cell death (e.g., apoptosis) in specified quantities. The cellular model may be simulated to monitor changes in the quantity of the components involved in cell death in response to external or internal species to determine if cell death would occur in the cell being modeled. The occurrence of cell death may be predicted by comparing the quantities of the components involved in cell death obtained in the simulation to the amounts seen in actual wild type cells undergoing cell death.

The compartments may be assigned to multiple parallel pathways within the same cellular model 102. Each compartment in the cellular model may be assigned to an unlimited number of pathways. Further, because compartments may be reused in different pathways within the same cellular model, a change to the contents of a compartment is reflected in any higher-level compartment within its designated pathway. In some embodiments, a change to a particular reaction, species, or compartment is made in all the parallel pathways to which the reaction, species or compartment is linked. This coupling of identical species and compartments is illustrated in FIG. 8 which shows, for example, that the parallel pathways for both cell 1 and cell 2 each include species I and II plus compartment A. Thus, in some embodiments, a change to species 1 in the parallel pathway of cell 1 would be reflected in the species 1 in the parallel pathway of cell 2.

In some embodiments, a reaction or a species in one compartment may be coupled with other identical species or reactions in other compartments to obtain coupled reactions or coupled species. A modification of the coupled reaction or coupled species may result in a similar modification of the other coupled species or other coupled reaction in the remaining compartments. In some embodiments, a modification of the coupled reaction or coupled species may result in an identical modification of the other coupled species or other coupled reaction in the remaining compartments.

The ability of some embodiments of the present invention to model parallel pathways makes them suited for modeling a group of cells, a single cell, or portions of cells. Thus, the compartments may represent a portion of a cell, a cell, or more than one cell.

Exemplary embodiments may be directed to techniques for modeling more than one cell using a single computer-implemented cellular model 102. In multicellular organisms, intercellular communication regulates cellular differentiation and growth patterns. Errors in this form of communication may lead to abnormalities, including cancer. Thus, designing and/or producing therapeutics capable of restoring normal cellular differentiation and growth patterns to abnormal cells (e.g., cancer cells) is a promising area of research for developing new therapeutics. Conventionally, researchers examine intercellular communication using in vitro assays in organisms such as *C. elegans, drosophila*, and *dictyostelium*. However, these assays may be laborious to perform and the supplies for each assay may be expensive.

Some embodiments in block 402 may alleviate this problem by providing an in silico means to model more than one cell in a single cellular model 102. These embodiments may be used to model intercellular communication in silico rather than in vitro. Each cell may be designated as a compartment or groups of cells may be designated as a compartment. In some embodiments, species and reactions may be added to the model.

This multicellular modeling may be used to examine communication between cells, i.e., intercellular communication, without having to construct an in vitro assay. For example, but not limited to, intercellular communication using a paracrine, autocrine, endocrine, or juxtacrine chemical messenger.

By designating the individual cells as compartments, the cellular model allows a user to switch between particular cells in a multicellular model without the need to create a new model. This may allow the user to create compartments with different species, for example, compartments with varying amounts or forms of the receptor activated by the intercellular messenger, within a single model. As the simulation is run in block 404, the user may switch between the different compartments to examine the effects the different species have on each compartment. In other embodiments, as the simulation is run in block 404, the simulation may automatically switch between the different compartments to simulate the effects the different species have on each compartment.

Exemplary embodiments may be used to model a single cell. When modeling a single cell, each compartment in the cellular model 102 may be a portion of the cell that is being modeled. For example, the compartments may represent an organelle, a membrane, or other physical region or item within the cell as the cell is being modeled. For example, the cellular model may be run to simulate the cell's response after an unnatural item (e.g., a viral genome) has been added to the cell. In some embodiments, species and reactions may be added to the model.

Exemplary embodiments may be used to model a portion of a cell. The cellular model 102 may represent only the portion of a cell that pertains to a desired cellular activity. For example, the cellular model may be constructed to simulate only cellular translation and transcription. This may allow the user to model the selected components of the cell needed for simulation without modeling the entire cell. As one of skill in the art will appreciate, this technique, as well as other techniques, of modeling a portion of a cell may be used to model individual pathways (e.g., apoptosis), collections of organelles, protein interaction within the cell, and any other model that does not require the construction of the entire cell for a simulation.

In some embodiments, the cellular model may include at least one compartment and at least one sub-compartment. For example, in a cellular model representing a group of cells each individual cell may be a compartment. The compartments within these compartments are sub-compartments. The use of sub-compartments within a cellular model of the present invention has been described previously and is illustrated by example in FIGS. 7A and 7B and FIGS. 8A and 8B.

Exemplary embodiments of the cellular model 102 may include multiple compartment hierarchies. Compartments may be used as building blocks within the cellular model to create any number of hierarchies within the cellular model. Each compartment in the cellular model may be assigned to an unlimited number of hierarchies. Further, because compartments may be reused in the present invention in different hierarchies within the same model, a change to the contents of a compartment may be reflected in any higher-level compartment within its designated hierarchies. In some embodiments, a change to a particular reaction, species, or compartment may be made in all hierarchies to which the reaction, species or compartment is linked.

Exemplary embodiments of the cellular model 102 may be used to simulate a cellular activity. Examples of a cellular activity may include: a cellular response pathway, a cellular signaling pathway, and a cellular metabolic pathway. In some embodiments, the cellular activity is selected from the group consisting of apoptosis, cell division, translation, transcription, glycolysis, the Krebs cycle, aerobic or anaerobic respiration, photosynthesis, and combinations thereof.

In some exemplary embodiments, the user may interact with the computing environment via a graphical user interface or a command line interface. The graphical user interface or the command line interface may be used to implement the methods of cellular modeling described herein.

Exemplary graphical user interfaces capable of being used in the present invention are provided in FIGS. 9-13. These graphical user interfaces allow the user to interact with the computing environment in the performance of the flowchart of FIG. 4. The graphical user interfaces of FIGS. 9-13 are intended to be exemplary and should not be construed as limiting the types of user interfaces, including graphical user interfaces, that can be used with techniques and/or embodiments disclosed herein.

Figure 9:
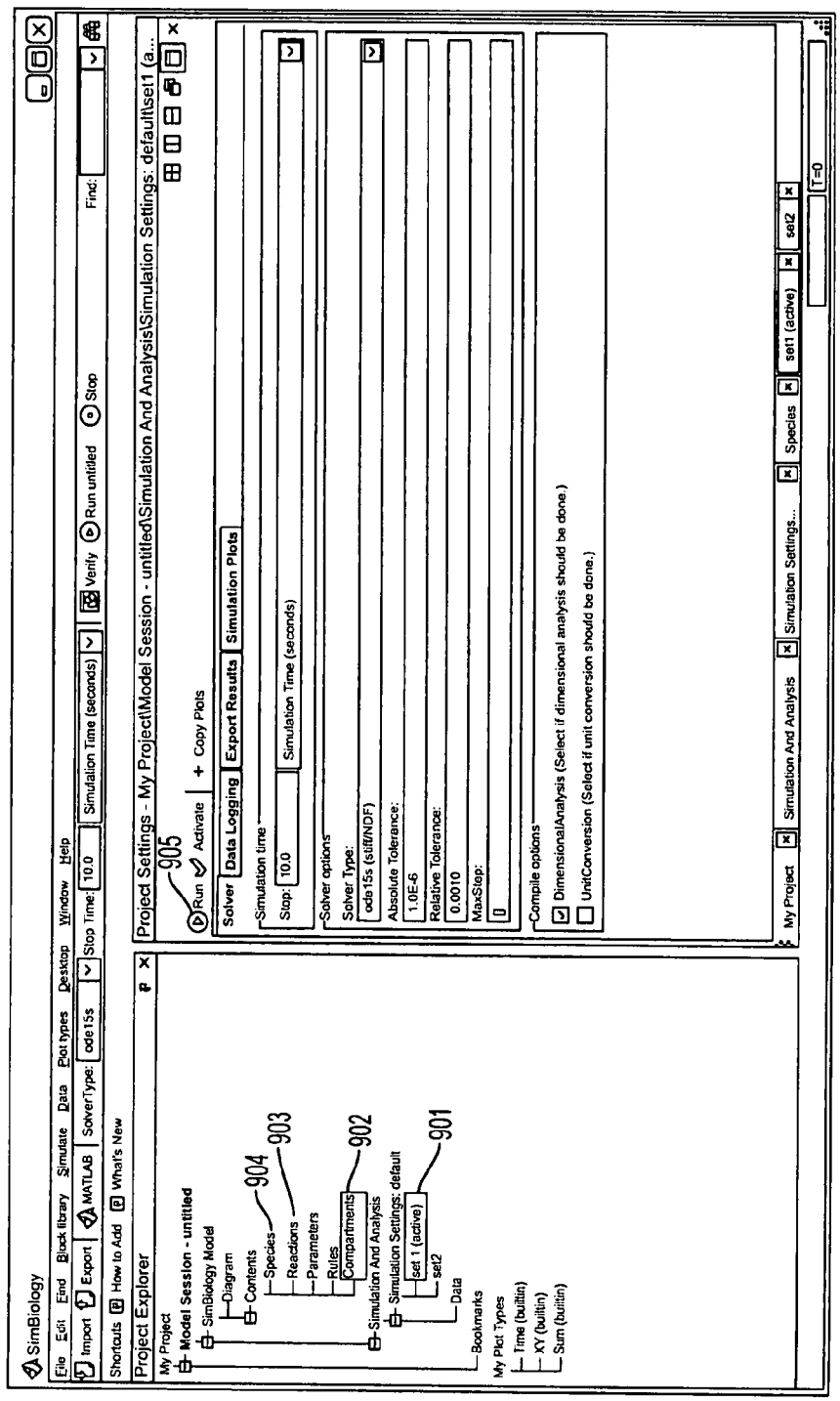
FIG. 9 illustrates an exemplary graphical user interface that may be used in a computer-implemented method of cellular modeling.
Figure 10:
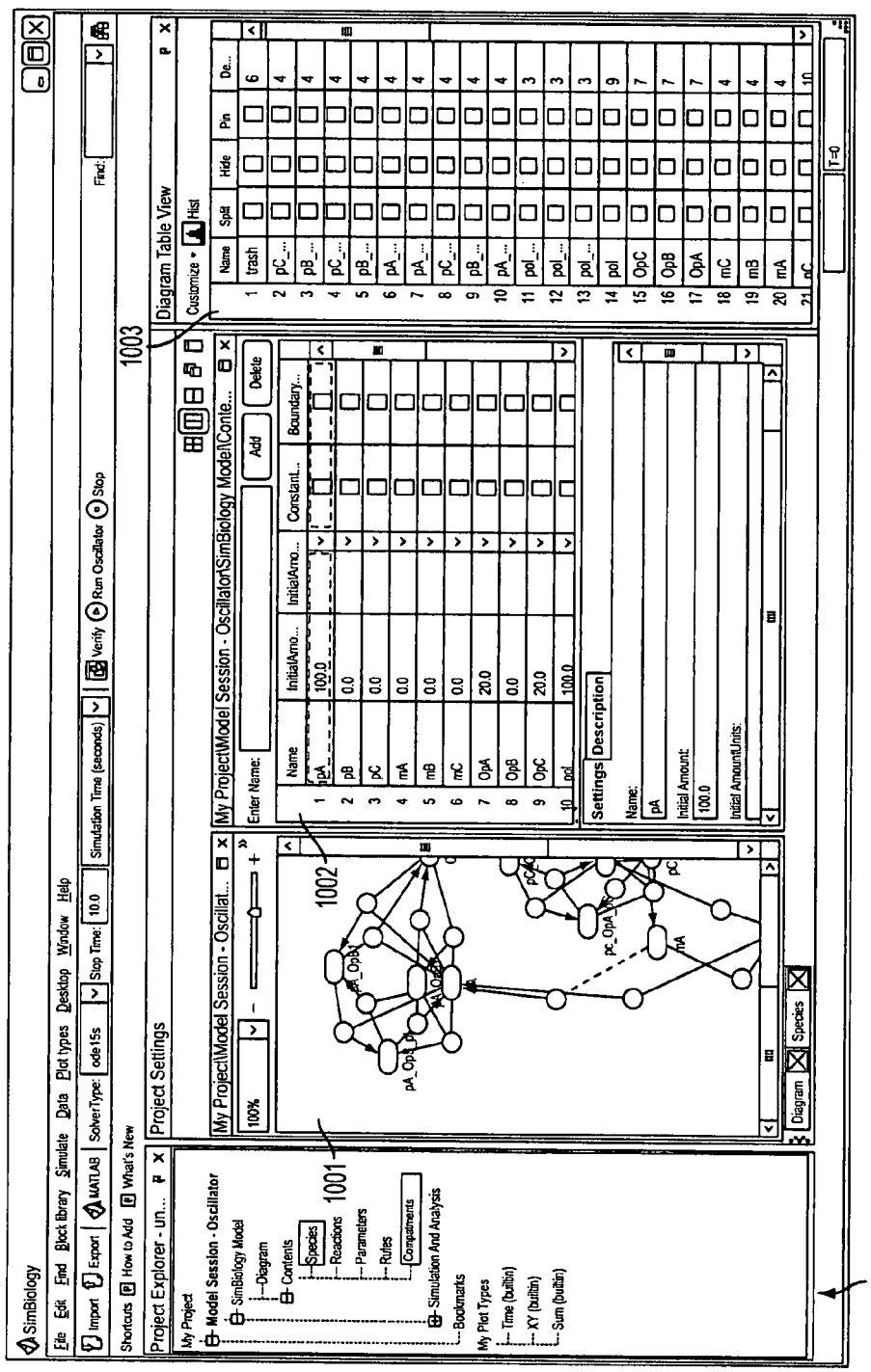
FIG. 10 illustrates an exemplary graphical user interface that may be used in a computer-implemented method of cellular modeling.

The graphical user interface depicted in FIG. 9 may include a listing where the species 904, reactions 903, or compartments 902 may be selected. Such a listing may be a tree-like structure as shown in FIG. 9. The selection of one or more species 904, reactions 903, or compartments 902 allows the user to visualize all items or only selected items within the cellular model 102. This selection is shown in more detail in FIG. 10 where the species have been selected for display in a table 1002 and in the graphical view 1001. The table 1002 allows the addition and deletion of the selected item (e.g., the species) from within the cellular model 1001. To further customize the display, the diagram table view 1003 contains a customization menu.

Referring back to FIG. 9, the listing may also contain the simulation settings received by the computing environment. For example, the simulations settings 901 of "set 1" is included here. The graphical user interface may include a run button 905 that may be used to begin the simulation of the cellular model in block 404.

Figure 11:
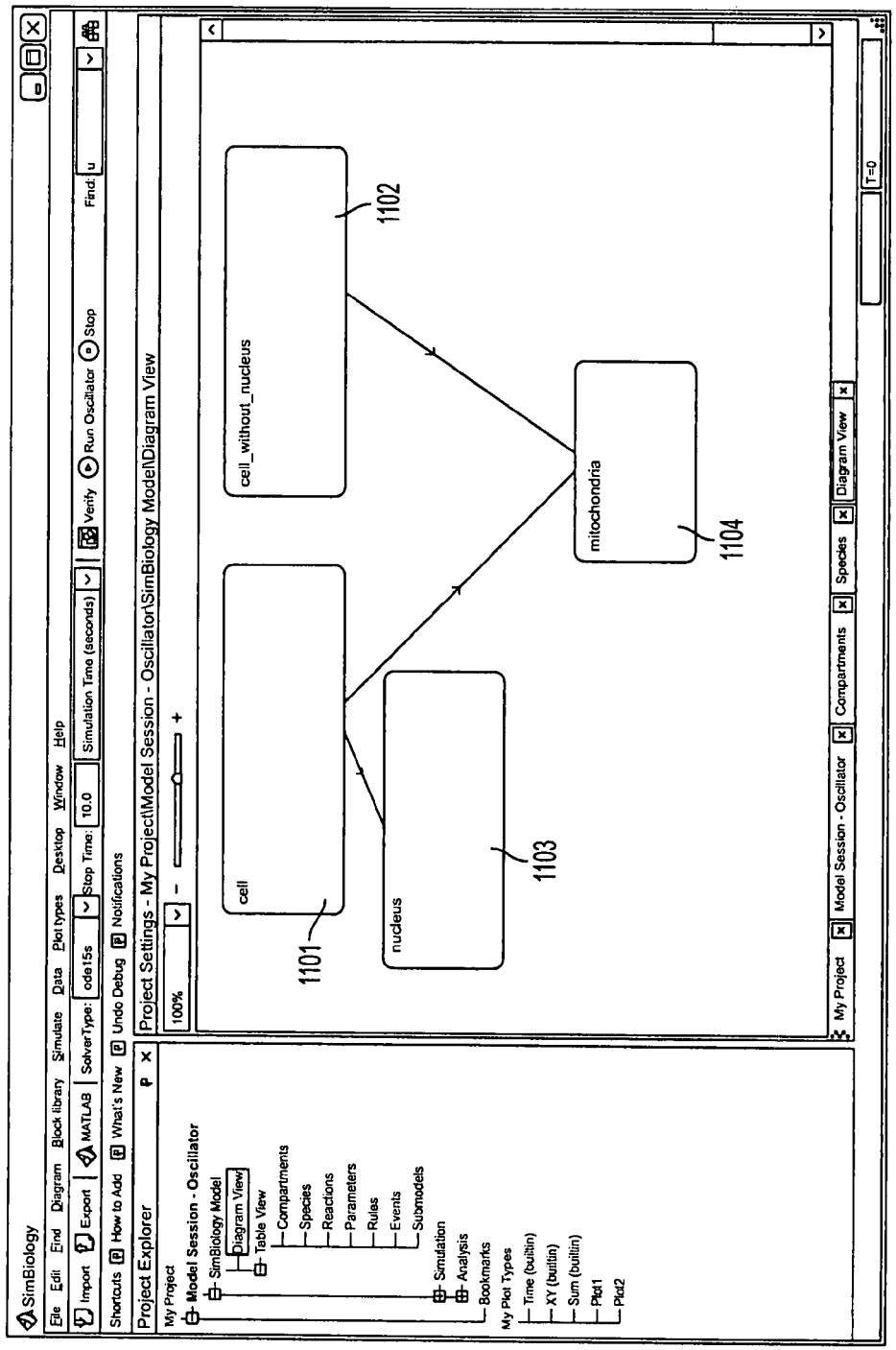
FIG. 11 illustrates an exemplary graphical user interface that may be used in a computer-implemented method of cellular modeling.

FIG. 11 shows a graphical user interface that displays the relationships between the components of the cellular model. One compartment 1101 is part of a parallel pathway called "cell" that includes a nucleus 1103 and a mitochondria 1104. A second compartment 1102 is part of a parallel pathway called "cell without nucleus" that contains the mitochondria 1104 but not the nucleus 1103. The graphical user interface can be used to change the relationships between the components of the cellular model being displayed.

Figure 12:
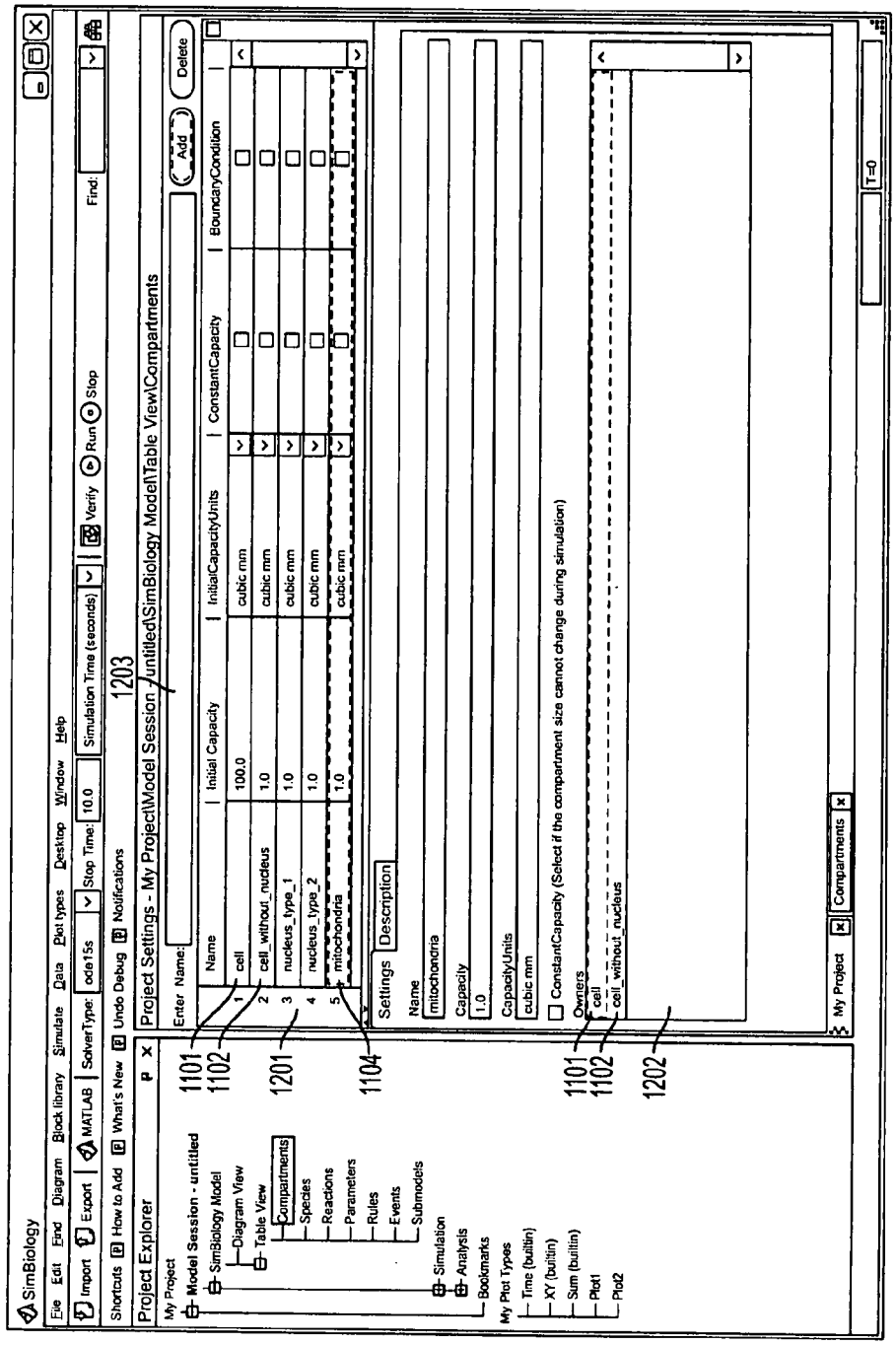
FIG. 12 illustrates an exemplary graphical user interface that may be used in a computer-implemented method of cellular modeling.

FIG. 12 shows a graphical user interface that displays a list of the available parallel pathways 1201. For example, note that the list 1201 contains the parallel pathway "cell" 1101 and the parallel pathway "cell without nucleus" 1102, previously illustrated in FIG. 11 in a different format. FIG. 12 also shows that displaying the mitochondria compartment 1104 in the listing will display a listing 1202 of the parallel pathways to which this compartment belongs. As indicated in the listing 1202, the mitochondria compartment 1104 belongs to both the parallel pathway of the cell 1101 and the cell without a nucleus 1102.

FIG. 12 also shows that the user can enter information into the cellular model using the box at 1203. This information may be entered into the model where it will be displayed in the list at 1201. Here the cell without nucleus parallel pathway 1102 is entered.

Figure 13:
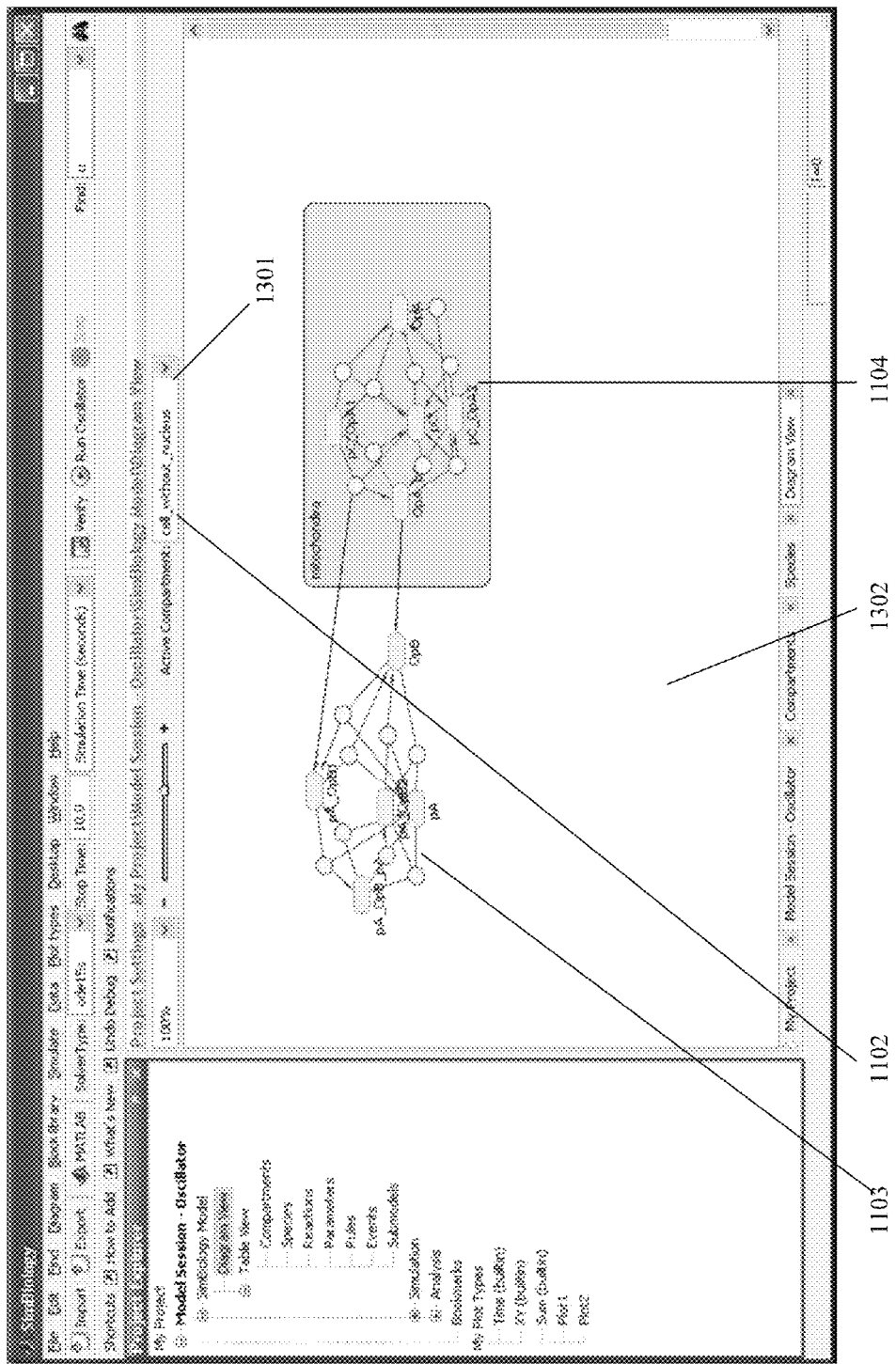
FIG. 13 illustrates an exemplary graphical user interface that may be used in a computer-implemented method of cellular modeling.

FIG. 13 shows a graphical user interface that is graphically displaying components of the cellular model. The graphical user interface allows the active compartment to be selected for display using box 1301. The area 1302 shows the cellular model containing the nucleus compartment 1103 and the mitochondria compartment 1104 of the cellular model. Box 1301 indicates a selection of the "cell without nucleus" parallel pathway 1102, and the mitochondria compartment 1104 is selected accordingly.

Exemplary embodiments may be further directed to computer-readable media including the computer-implemented cellular models described herein. In some embodiments, the computer-readable medium includes the computer-implemented models described herein as software.

Exemplary embodiments may also be directed to kits containing the computer-readable media of the present invention. In some embodiments, the kit may be a box, a bag, a pouch, a Compact Disc (CD) jewel case, a shrink wrapped container, or any another suitable container with the computer-readable medium inside it.

The kits may also contain items in addition to the computer-readable media. For example, the kits may further comprise a book, pamphlet, instructions, a DVD, a CD-ROM, an audio CD, a video tape, an audio cassette, testing supplies, or a live organism.

Exemplary embodiments are also directed to systems for manufacturing a biological product. The computer-implemented cellular modeling programs may be coupled to a manufacturing system for constructing a biological product. The compositions and properties of the components simulated in the cellular model may be transferred to the manufacturing system in the form of data. Upon receiving the cellular model data, the manufacturing system may create a real life version of the item being modeled. For example, a manufacturing system might inject cells with a cancer therapeutic in accordance with the data received by the cellular modeling program that has modeled these cells with the therapeutic to produce in vitro data of the cellular model's simulation. These embodiments may allow in silico and in vitro data to be rapidly gathered on a large scale using automated systems.

Accordingly, exemplary embodiments may be directed to a system for manufacturing a biological product, the system including a cellular modeling environment. The cellular modeling environment may include a program for cellular modeling. The program may be used to implement the methods of cellular modeling described herein. The cellular modeling environment may be coupled to a manufacturing system capable of manufacturing a biological product based on the cellular model. The cellular modeling environment and the manufacturing system may be implemented, for example, with the same computer system or separate ones connected via a network.

Exemplary embodiments may be directed to a distributed computing system for cellular modeling. The distributed system may include a remote computing site that may contain a cellular modeling environment. The cellular modeling environment may be used to implement the methods of cellular modeling described herein. The distributed system may also include a client computing site capable of interacting with the remote computing site to obtain an output. The remote computing site and the client site may be implemented, for example, with separate computer systems connected via a network.

The distributed computing system may be controlled using a manager computing device. The manager computing device may control access to the remote computing site. The manager computing device may be a computer or a computer system.

For example, the manager computing device may determine via a check if the license of the client computing site is valid or if access to the remote computing site should be permitted. The manager computing device may determine via a check if the client computing site has paid for access. If the client computing site has paid, the manager computing device may permit access to the remote computing site. Payment for access may be made on a subscription basis or on a per use basis.

Disclosed examples and exemplary embodiments illustrate possible embodiments and/or techniques that can be used to practice aspects of the invention. As one of skill in the art will appreciate, because of the versatility of the techniques and/or embodiments of modeling cell(s) or portions of cells, the invention disclosed herein may be used to simulate a wide array of biochemical pathways and/or cellular activities.

Thus, while the invention has been particularly shown and described with reference to some embodiments thereof, it will be understood by those skilled in the art that they have been presented by way of example only, and not limitation, and various changes in form and details may be made therein without departing from the spirit and scope of the invention. Therefore, the breadth and scope of the present invention should not be limited by any of the above-described exemplary embodiments, but should be defined only in accordance with the following claims and their equivalents.

What is claimed is:

1. A computer-implemented method for cellular modeling comprising:

generating a cellular model including a plurality of compartments, the cellular model including at least a first compartment, a second compartment, and a third compartment from the plurality of compartments, the first compartment and the second compartment being variations of the third compartment, the first compartment and the second compartment having a shared portion, the shared portion including at least one of a shared compartment from the plurality of compartments shared by the first compartment and the second compartment, the first compartment having an unshared portion, the unshared portion including at least one of an unshared compartment from the plurality of compartments, a reaction, or a species not shared by the second compartment;

receiving a selection of a portion of the cellular model to simulate, the selected portion of the cellular model comprising at least one of: the first compartment, the second compartment, or a combination of the first compartment and the second compartment;

simulating, using a processor, the cellular model including the selected portion of the cellular model to obtain a result; and providing an output, the output comprising the result from simulating the selected portion of the cellular model.

2. The method of claim 1, wherein the shared species of the cellular model comprises at least one of a peptide, a polypeptide, a nucleotide, or a polynucleotide.

3. The method of claim 1, wherein the shared species of the cellular model comprises at least one of an ion, an acid, a base, a salt, or a prodrug.

4. The method of claim 1, wherein at least one of the plurality of compartments of the cellular model represents an object comprising at least one of a plurality of cells, a single cell, or a portion of a cell.

5. The method of claim 4, wherein the portion of a cell is an organelle.

6. The method of claim 1, wherein the cellular model represents a cellular activity comprising at least one of a cellular response pathway, a cellular signaling pathway, or a cellular metabolic pathway.

7. The method of claim 1, wherein the cellular model represents a cellular activity comprising at least one of apoptosis, cell division, translation, transcription, glycolysis, the Krebs cycle, aerobic or anaerobic respiration, or photosynthesis.

8. The method of claim 1, wherein the cellular model represents an intercellular signaling mechanism.

9. The method of claim 1, further comprising:
identifying a selection of a compartment; and
displaying the identified compartment.

10. The method of claim 1, further comprising:
displaying the cellular model in a graphical user interface or a command line format.

11. The method of claim 1, further comprising:
displaying at least one of the plurality of compartments in a graphical user interface or a command line format.

12. A method of cellular modeling comprising:
downloading software to a computer system, which when the software is executed by the computer system, causes the computer system to perform operations comprising the method of claim 1.

13. The method of claim 1, wherein the first variation models a cell in the presence of a species and the second variation models a cell in the absence of said species, and the cellular model is simulated to produce a result that compares the effect of the addition of said species.

14. The method of claim 13, wherein the species is a therapeutic agent.

15. The method of claim 1, wherein the first variation models a cell with the presence of a particular sub-compartment having wild-type components and the second compartment models a cell with additional altered forms of the sub-compartment with mutant or unnatural components, and the cellular model is simulated to produce a result that compares the effect of the additional sub-compartments.

16. The method of claim 1, further comprising:
providing to a user at least an option to simulate the cellular model either with the first compartment, the second compartment, or with the first and second compartments.

17. A non-transitory computer-readable medium comprising code for a computer-implemented method of cellular modeling, the code comprising instructions for:
generating a cellular model including a plurality of compartments, the cellular model including at least a first compartment, a second compartment, and a third compartment from the plurality of compartments, the first compartment and the second compartment being variations of the third compartment, the first compartment and the second compartment having a shared portion, the shared portion including at least one of a shared compartment from the plurality of compartments shared by the first compartment and the second compartment, the first compartment having an unshared portion, the unshared portion including at least one of an unshared compartment from the plurality of compartments, a reaction, or a species not shared by the second compartment;

receiving a selection of a portion of the cellular model to simulate, the selected portion of the cellular model comprising at least one of: the first compartment, the second compartment, or a combination of the first compartment and the second compartment;

simulating the cellular model including the selected portion of the cellular model to obtain a result; and outputting the result from simulating the selected portion of the cellular model.

18. A computer-implemented method for modeling a synthetic cell comprising:
generating, using a processor, a cellular model of a synthetic cell including a plurality of compartments, the cellular model including at least a first compartment, a second compartment, and a third compartment from the plurality of compartments, the first compartment and the second compartment being variations of the third compartment, the first compartment and the second compartment having a shared portion, the shared portion including at least one of a shared compartment from the plurality of compartments shared by the first compartment and the second compartment, the first compartment having an unshared portion, the unshared portion including at least one of a an unshared compartment from the plurality of compartments, a reaction, or a species not shared by the second compartment and not being found in a natural cell;

receiving a selection of a portion of the cellular model to simulate, the selected portion of the cellular model comprising at least one of: the first compartment, the second compartment, or a combination of the first compartment and the second compartment;

simulating the cellular model including the selected portion of the cellular model to obtain a result; and providing an output, the output comprising the result from simulating the selected portion of the cellular model.

19. The method of claim 18, further comprising:
identifying a selection of a compartment; and
displaying the identified compartment.

20. The method of claim 18, further comprising:
displaying the cellular model in a graphical user interface or a command line format.

21. The method of claim 18, wherein the first compartment models a cell in the presence of a species and the second compartment models a cell in the absence of said species, and the cellular model is simulated to produce a result that compares the effect of the addition of said species.

22. The method of claim 21, wherein the species is a therapeutic agent.

23. The method of claim 18, wherein the first compartment models a cell with the presence of a particular sub-compartment having wild-type components and the second compartment models a cell with additional altered forms of the sub-compartment with mutant or unnatural components, and the cellular model is simulated to produce a result that compares the effect of the additional sub-compartments.

24. A system for cellular modeling comprising:
a graphical user interface to interact with a computer implemented cellular model; and
a processor coupled to the graphical user interface, the processor for:
generating the cellular model including a plurality of compartments, the cellular model including at least a first compartment, a second compartment, and a third compartment from the plurality of compartments, the first compartment and the second compartment being variations of the third compartment, the first compartment and the second compartment having a shared portion, the shared portion including at least one of a shared compartment from the plurality of compartments shared by the first compartment and the second compartment, the first compartment having an unshared portion, the unshared portion including at least one of an unshared compartment from the plurality of compartments, a reaction, or a species not shared by the second compartment;
receiving a selection of a portion of the cellular model to simulate, the selected portion of the cellular model comprising at least one of: the first compartment, the second compartment, or a combination of the first compartment and the second compartment;
simulating the cellular model including selected portion of the cellular model to obtain a result; and
outputting the result on the user interface.

* * * * *